United States Patent [19]

Lekholm et al.

[11] Patent Number: 4,840,186
[45] Date of Patent: Jun. 20, 1989

[54] IMPLANTABLE MULTI-POLE COAXIAL LEAD

[75] Inventors: Anders Lekholm, Bromma; Ulf Fahlstroem, Stockholm, both of Sweden; Hermann Groothoff, Friesoythe/Altenoythe, Fed. Rep. of Germany

[73] Assignee: Siemens Aktiengesellschaft, Munich, Fed. Rep. of Germany

[21] Appl. No.: 199,920

[22] Filed: May 27, 1988

[30] Foreign Application Priority Data

Jun. 1, 1987 [EP] European Pat. Off. ........ 87107895.2

[51] Int. Cl.⁴ .............................................. A61N 1/00
[52] U.S. Cl. .............................. 128/784; 128/419 P; 128/786
[58] Field of Search ............ 128/783, 784, 419 P, 128/786, 785, 642

[56] References Cited

U.S. PATENT DOCUMENTS

| 3,596,662 | 8/1971 | Bolduc | 128/786 |
| 4,106,512 | 8/1978 | Bisping | 128/419 P |
| 4,327,747 | 5/1982 | Gold | 128/784 |
| 4,559,951 | 12/1985 | Dahl et al. | 128/642 |
| 4,590,950 | 5/1986 | Iwaszkiewicz et al. | 128/786 |
| 4,640,983 | 2/1987 | Comte | 128/784 |

FOREIGN PATENT DOCUMENTS

| 0092798 | 4/1983 | European Pat. Off. | |
| 2408707 | 2/1973 | Fed. Rep. of Germany . | |
| 3031752 | 8/1980 | Fed. Rep. of Germany . | |
| 656313 | 12/1978 | Switzerland . | |
| 8002231 | 10/1980 | World Int. Prop. O. | 128/419 P |
| 8304182 | 12/1983 | World Int. Prop. O. | 128/784 |

*Primary Examiner*—Lee S. Cohen
*Assistant Examiner*—K. Schaetzle

[57] ABSTRACT

An implantable lead has conductors wound in a multi-pole helix. The conductors are individually insulated by a first insulating material and the insulated conductors are embedded in, and axially separated from each other by a second tube-formed insulating material. The inner opening of the tube receives a helically wound stylet guide coil which may also be a multi-pole conductor arrangement. The conductors may be helically wound, multi-filament wires. Preferably, all helically wound arrangements in the lead are wound in the same direction so that the lead is still when rotating it in one direction and flexible when rotating it the other way.

17 Claims, 1 Drawing Sheet

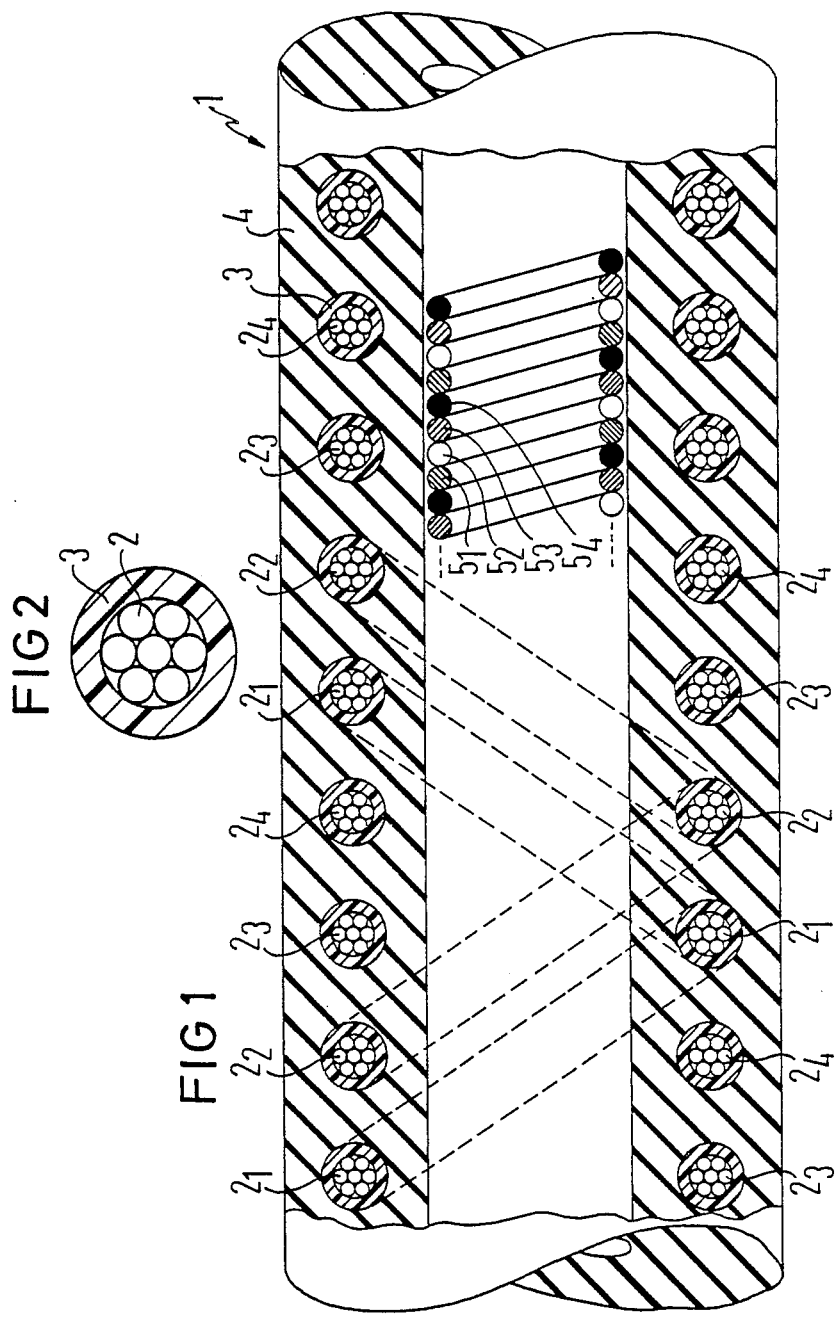

IMPLANTABLE MULTI-POLE COAXIAL LEAD

BACKGROUND OF THE INVENTION

1. Field of the Invention

The present invention relates to an implantable multi-pole coaxial lead or cable of the type suitable for use in an electrode arrangement for stimulating intracardiac tissue in a pacer system.

2. Description of the Prior Art

The demands on a multi-pole coaxial lead for use as part of an implanted electrode arrangement in systems such as heart pacemakers with a long life time are extremely high. A lead of this type must be body compatible, of low resistance to maintain energy consumption at a low level thereby increasing life time of pacemaker batteries, exhibit a high fatigue strength under repeated bending stresses, pliant in order to cause minimum disruptions to surrounding organs, as well as stiff enough when pushed forward to enable an easy insertion by the physician.

Moreover, these demands are at least in part contradicting as is obviously the case for pliant and low resistance requirements. In order to be pliant the conductors of the lead should essentially have a small diameter and in order to be of low resistance the conductors should have a larger diameter.

The attempts to overcome these difficulties in the past are manifold. A coaxial lead is disclosed in German OS No. 3 031 752 wherein the conductors are individually insulated and wound into a single multi-pole helix. Although the diameter of this lead is reduced in comparison to a lead with an inner and an outer helix of conductors separated from another by an insulating sheath and the conductors also being surrounded at the exterior of the lead by a further insulating sheath, the multi-pole helix necessarily has a steeper pitch and thus exhibits reduced flexibility. Further, the single insulating material requires a compromise between the electric properties and body compatibility for that material.

In European Application No. 92 798 a lead is disclosed wherein the outer helix is a metal tape or tape-shaped cord in order to reduce diameter and resistance while increasing flexibility.

A multi-pole lead for catheters and electrical measurements in the medical field is exemplified in German OS No. 2 408 707 in which a multi-pole helix of axially separated conductors with a first insulating material is further insulated by disposing the helix in the wall of a tube-formed second insulating material. The interior of the tube is a fluid conduit. Although this arrangement where the conductors and the first insulating material are embedded in the second insulating material achieves having a reduced diameter as well as good electrical insulating and body compatibility properties, the explicitly stated materials for the conductor, copper, and for the first insulating material, insulating paint, have properties which make this lead unsuitable for implantation, especially intracardial implantation. The materials in a lead for intracardial implantation must withstand around 100,000 flexes a day, and consequently the lead must exhibit an extremely high fatigue strength, which copper does not satisfy. Further, if a stylet were used at insertion, insulating paint is unsuitable because the walls of insulating material in the central opening of the lead could easily be penetrated.

SUMMARY OF THE INVENTION

It is an object of the present invention to provide an implantable multi-pole coaxial lead presenting an optimal compromise to the diverging requirements for stiffness, flexibility, fatigue strength and resistance discussed in the preceding paragraphs.

The above and other objects are achieved in accordance with the principles of the present invention in a multi-pole lead having a helix of individually insulated conductors embedded in the wall of the lead tubing, with the inner opening of the tubing receiving a helically wound stylet guide coil. The lead exhibits reduced diameter, good electrical and body compatibility properties in combination with a stylet guide member protective against penetration.

Preferably, the stylet guide coil consists of individually insulated conductors in a multi-pole arrangement to increase the versatility of the lead.

Preferably, to increase flexibility of the lead, at least one conductor embedded in the lead tubing is a wire consisting of helically wound multiple filaments. Additionally or alternatively, if the guide coil consists of a plurality of conductors, at least one of those conductors may consist of helically wound multiple filaments.

Preferably, in order to further improve lead properties at insertion, all helices in the lead are wound in the same (left or right hand) direction. This preferable embodiment corresponds to the habit of surgeons to insert the lead so that the forward direction of the lead includes helical movement of the surgeon's hand in one direction, and withdrawal of the lead includes a movement of the surgeon's hand in the opposite direction. As it is preferable that the lead is flexible at withdrawal from the fixation tissue and stiff when approaching the fixation tissue, and several attempts may be required before an optimal electrode fixation is achieved, it is of great importance that this is an intrinsic property of the lead irrespective of stylet function. This is achieved by arranging all helices (i.e., the helix embedded in the tubing, the guide coil stylet helix, and the multiple filament helices) in the same direction, viz., for right handed surgeons the helices should be wound in the left hand direction and for left handed surgeons the helices should be wound in the right hand direction.

Other embodiments of the invention are directed to combinations of conductor and insulating materials.

DESCRIPTION OF THE DRAWINGS

FIG. 1 is an axial sectional view of a multi-pole coaxial lead constructed in accordance with the present invention illustrating a four-pole conductor arrangement embedded in an insulating tube of silicone rubber, with a four-pole stylet guide coil arrangement.

FIG. 2 is a radial sectional view of a helically wound multi-filament conductor.

DESCRIPTION OF THE PREFERRED EMBODIMENTS

Referring to the figures, an embodiment of the invention includes a multi-pole lead 1 having outer helically wound conductors 2 in a four-pole arrangement $2_1$, $2_2$, $2_3$, $2_4$. The conductors 2 consist of multi-filament (e.g., refined steel) wire exhibiting high fatigue strength under repeated flexing stress. The filaments are all wound in the same direction. The conductors are surrounded by a first insulating material 3 with good electric insulating properties, such as FEP (fluorinated ethylene propylene) or PTFE (polytetrafluoroethylene). The conductors are embedded in a second insulating material 4 with good body compatibility properties, e.g., silicone rubber such as silastic Q7-4840 produced by Dow Corning Company. The insulating material 4 is in the form of a tube having a central opening in which a stylet guide coil 5 arranged as a multi-pole conductor arrangement $5_1$, $5_2$, $5_3$, $5_4$. The guide coil conductors may consist of MP 35 N, possibly in a multi-filament arrangement.

The conductors 2 and 5 may each be individually identified by colored insulation material, possibly combined with an X-ray contrast medium. By way of example, the guide coil 5 may have an inner diameter of about 0.5 mm and the lead may have an outer diameter of about 2.0 mm. The outer conductor helix is wound with a pitch of 2 to 4 mm, and the distance between the insulated conductors is around 0.2 mm. The tube-formed second insulating material 4 is produced in two steps. The first step is extrusion of the inner part of the tube, and the second step is extrusion of the outer part of the tube over the insulated outer conductors 2 wound on the extruded inner part of the tube, so that the outer conductor helix is embedded in the thus-formed integrated tube wall.

The described embodiment could be modified to accomodate various other pole arrangements of the conductors in the outer and in the guide coil helices.

Although modifications and changes may be suggested by those skilled in the art it is the intention of the inventors to embody within the patent warranted hereon all changes and modifications as reasonably and properly come within the scope of their contribution to the art.

We claim as our invention:

1. A multi-pole coaxial lead for an electrode for stimulating body tissue comprising:
a plurality of conductors wound in a helix; first insulating material individually surrounding each conductor in said plurality of conductors;
a tube consisting of a second insulating material said tube having a wall in which said plurality of conductors are embedded and axially separated from each other surrounded by said second insulating material, and said tube having a central opening therein; and
a helically wound stylet guide coil disposed in said central opening of said tube of second insulating material.

2. A multi-pole coaxial lead as claimed in claim 1, wherein at least one conductor in said plurality of conductors is a multi-filament wire.

3. A multi-pole coaxial lead as claimed in claim 2, wherein the filaments in said multi-filament wire are helically wound.

4. A multi-pole coaxial lead as claimed in claim 3, wherein said plurality of conductors embedded in said second insulating material, said stylet guide coil, and said filaments are all helically wound in the same direction.

5. A multi-pole coaxial lead as claimed in claim 1, wherein said stylet guide coil at least partially consists of electrically conducting material.

6. A multi-pole coaxial lead as claimed in claim 1, wherein said stylet guide coil consists of a multi-pole arrangement of a further plurality of conductors.

7. A multi-pole coaxial lead as claimed in claim 6, wherein at leat one of said conductors in said further plurality of conductors is a multi-filament wire.

8. A multi-pole coaxial lead as claimed in claim 7, wherein the filaments in said multi-filament wire are helically wound.

9. The multi-pole coaxial lead as claimed in claim 8, wherein said plurality of conductors embedded in said second insulating material, said stylet guide coil, and said filaments are all helically wound in the same direction.

10. A multi-pole coaxial lead as claimed in claim 1, wherein said first insulating material consist of material selected from the group consisting of fluorinated ethylene propylene or polytetrafluoroethylene.

11. A multi-pole coaxial lead as claimed in claim 1, wherein said second insulating material consists of silicone rubber.

12. A multi-pole coaxial lead as claimed in claim 1, wherein said first insulating material includes means for individually identifying the conductors in said plurality of conductors.

13. A multi-pole coaxial lead as claimed in claim 12, wherein said means for identifying is a plurality of different colors of said first insulating material, each color being associated with one conductor in said plurality of conductors.

14. A multi-pole coaxial lead as claimed in claim 12, wherein said means for identifying is an x-ray contrast medium having a different contrast for each conductor in said plurality of conductors.

15. A multi-pole coaxial lead as claimed in claim 12, wherein said means for identifying is a combination of differently colored first insulating material and x-ray contrast medium, with a different color and a different contrast being associated with each conductor in said plurality of conductors.

16. A multi-pole coaxial lead for an electrode for stimulating body tissue comprising:
a first plurality of conductors wound in a helix;
first insulating material individually sourrounding each conductor in said first plurality of conductors;
a tube consisting of second insulating material having a tube wall in which said helix of said first plurality of conductors is embedded, with the conductors of said first plurality of conductors being axially separated from each other by said second insulating material, said tube having a central opening therein; and
a stylet guide coil disposed in said central opening of said tube, said stylet guide coil consisting of a second plurality of conductors wound in a helix, said helix of said first plurality of conductors and said helix of said second plurality of conductors being wound in the same direction.

17. A multi-pole coaxial lead for an electrode for stimulating body tissue comprising:
a first plurality of conductors wound in a first helix, at least one conductor in said first plurality of conductors consisting of multi-filament wire with the filaments of said multi-filament wire wound in a second helix;
first insulating material individually surrounding each conductor in said first plurality of conductors; a tube consisting of second insulating material having a tube wall in which said first helix of said first plurality of conductors is embedded with the conductors in said first plurality of conductors being axially separated from each other by said second insulating material, said tube having a central opening;

a stylet guide coil disposed in said central opening of said tube, said stylet coil consisting of a second plurality of conductors wound in a third helix, at least one conductor in said second plurality of conductors consisting of multi-filament wire with the filaments of said multi-filament wire wound in a fourth helix; and said first, second, third and fourth helices being wound in the same direction.

* * * * *